(12) United States Patent
Etminan (10) Patent No.: US 9,402,736 B2
(45) Date of Patent: Aug. 2, 2016

(54) INTERBODY FUSION IMPLANT AND RELATED METHODS

(71) Applicant: Alphatec Spine, Inc., Carlsbad, CA (US)

(72) Inventor: Mohammad Etminan, Houston, TX (US)

(73) Assignee: Alphatec Spine, Inc., Carlsbad, CA (US)

( * ) Notice: Subject to any disclaimer, the term of this patent is extended or adjusted under 35 U.S.C. 154(b) by 281 days.

(21) Appl. No.: 14/026,364

(22) Filed: Sep. 13, 2013

(65) Prior Publication Data

US 2014/0088710 A1    Mar. 27, 2014

Related U.S. Application Data

(60) Provisional application No. 61/705,314, filed on Sep. 25, 2012.

(51) Int. Cl.
*A61F 2/44* (2006.01)
*A61F 2/30* (2006.01)
*A61F 2/28* (2006.01)
*A61F 2/46* (2006.01)

(52) U.S. Cl.
CPC ............ *A61F 2/4455* (2013.01); *A61F 2/30744* (2013.01); *A61F 2002/2835* (2013.01); *A61F 2002/30476* (2013.01); *A61F 2002/30578* (2013.01); *A61F 2002/4677* (2013.01)

(58) Field of Classification Search
CPC ......... A61F 2/44; A61F 2/4455; A61F 2/446; A61F 2/4465; A61F 2/447; A61F 2/46; A61F 2/4603; A61F 2/4611; A61F 2002/2835; A61F 2002/30747; A61F 2002/4475; A61F 2002/464
See application file for complete search history.

(56) References Cited

U.S. PATENT DOCUMENTS

| | | | | |
|---|---|---|---|---|
| 5,397,364 A * | 3/1995 | Kozak | ................... | A61B 17/025 606/247 |
| 5,683,394 A * | 11/1997 | Rinner | ................... | A61F 2/4455 606/247 |
| 6,200,347 B1 * | 3/2001 | Anderson | ................... | A61F 2/28 623/11.11 |
| 6,964,687 B1 * | 11/2005 | Bernard | ................... | A61F 2/447 623/17.11 |
| 7,232,463 B2 * | 6/2007 | Falahee | ............... | A61B 17/1757 623/17.11 |
| 7,674,297 B2 * | 3/2010 | Falahee | ................... | A61F 2/4455 623/17.11 |
| 7,726,002 B2 * | 6/2010 | Shimp | ...................... | A61F 2/28 29/525.01 |
| 8,088,163 B1 * | 1/2012 | Kleiner | ................... | A61F 2/4465 623/17.11 |
| 8,268,000 B2 * | 9/2012 | Waugh | ................... | A61F 2/4465 623/17.16 |
| 8,277,510 B2 * | 10/2012 | Kleiner | ................... | A61F 2/4465 606/86 A |
| 8,292,960 B2 * | 10/2012 | Kleiner | ................... | A61F 2/4465 623/17.11 |
| 8,333,804 B1 * | 12/2012 | Wensel | ................ | A61B 17/864 623/17.11 |

(Continued)

*Primary Examiner* — Christian Sevilla
*Assistant Examiner* — Eric S Gibson
(74) *Attorney, Agent, or Firm* — Alphatec Spine, Inc.

(57) ABSTRACT

An interbody fusion implant system according to the principles of the present disclosure includes a base member, a first guide, a second guide, and a closure member with a first thru-bore and a second thru-bore. The base member includes a first side wall, a second side wall, and an end wall to define an open trailing end and an interior bounded by the side walls and the end wall. Each guide includes length and has a first portion attached to the proximal end of the first side wall and a second portion extending freely away from the first portion. The closure member includes a first thru-bore configured to be received by the first guide to align the closure member with the first side wall and a second thru-bore configured to be received by the second guide to align the closure member with the second side wall.

15 Claims, 4 Drawing Sheets

(56) References Cited

U.S. PATENT DOCUMENTS

| | | | | |
|---|---|---|---|---|
| 8,382,839 B1* | 2/2013 | Wensel | A61B 17/864 | 623/17.11 |
| 8,460,385 B1* | 6/2013 | Wensel | A61B 17/864 | 623/17.11 |
| 8,480,747 B2* | 7/2013 | Melkent | A61F 2/442 | 623/17.11 |
| 8,491,658 B1* | 7/2013 | Etminan | A61F 2/442 | 623/17.16 |
| 8,523,945 B1* | 9/2013 | Wensel | A61B 17/864 | 623/17.11 |
| 8,523,946 B1* | 9/2013 | Swann | A61F 2/447 | 623/17.11 |
| 8,551,175 B1* | 10/2013 | Wensel | A61F 2/447 | 623/17.11 |
| 8,715,355 B2* | 5/2014 | Kleiner | A61F 2/4465 | 623/17.12 |
| 8,795,369 B1* | 8/2014 | Pimenta | A61B 17/1604 | 606/86 A |
| 8,808,305 B2* | 8/2014 | Kleiner | A61F 2/4465 | 606/105 |
| 8,864,654 B2* | 10/2014 | Kleiner | A61B 1/0607 | 600/104 |
| 8,900,307 B2* | 12/2014 | Hawkins | A61F 2/4455 | 623/17.16 |
| 8,932,358 B1* | 1/2015 | Nehls | A61F 2/4455 | 623/17.16 |
| 8,956,416 B2* | 2/2015 | McCarthy | A61F 2/4455 | 623/17.16 |
| 9,028,549 B1* | 5/2015 | Wensel | A61B 17/864 | 623/17.11 |
| 9,144,501 B1* | 9/2015 | Pimenta | A61B 17/1604 | |
| 9,155,631 B2* | 10/2015 | Seifert | A61F 2/442 | |
| 2002/0106393 A1* | 8/2002 | Bianchi | A61B 17/1637 | 424/423 |
| 2003/0004576 A1* | 1/2003 | Thalgott | A61F 2/4455 | 623/17.16 |
| 2004/0034430 A1* | 2/2004 | Falahee | A61F 2/4455 | 623/17.16 |
| 2004/0088055 A1* | 5/2004 | Hanson | A61B 17/1671 | 623/17.16 |
| 2004/0126407 A1* | 7/2004 | Falahee | A61B 17/1757 | 424/423 |
| 2005/0015151 A1* | 1/2005 | Fortin | A61F 2/442 | 623/17.13 |
| 2005/0065605 A1* | 3/2005 | Jackson | A61F 2/446 | 623/17.11 |
| 2005/0065606 A1* | 3/2005 | Jackson | A61F 2/446 | 623/17.11 |
| 2005/0143819 A1* | 6/2005 | Falahee | A61F 2/4455 | 623/17.11 |
| 2005/0240267 A1* | 10/2005 | Randall | A61F 2/44 | 623/17.11 |
| 2007/0093898 A1* | 4/2007 | Schwab | A61F 2/4465 | 623/17.11 |
| 2007/0156241 A1* | 7/2007 | Reiley | A61B 17/1615 | 623/17.11 |
| 2008/0249625 A1* | 10/2008 | Waugh | A61F 2/4465 | 623/17.16 |
| 2009/0005870 A1* | 1/2009 | Hawkins | A61F 2/4455 | 623/17.11 |
| 2009/0030519 A1* | 1/2009 | Falahee | A61B 17/1757 | 623/17.16 |
| 2011/0040384 A1* | 2/2011 | Junn | A61F 2/447 | 623/17.12 |
| 2011/0098747 A1* | 4/2011 | Donner | A61B 17/70 | 606/264 |
| 2011/0137417 A1* | 6/2011 | Lee | A61F 2/4455 | 623/16.11 |
| 2011/0230968 A1* | 9/2011 | Perisic | A61F 2/447 | 623/17.16 |
| 2011/0270318 A1* | 11/2011 | Michelson | A61B 17/025 | 606/279 |
| 2012/0059477 A1* | 3/2012 | Kleiner | A61F 2/4465 | 623/17.16 |
| 2012/0065688 A1* | 3/2012 | Nehls | A61B 17/7059 | 606/279 |
| 2012/0172989 A1* | 7/2012 | McCarthy | A61F 2/4455 | 623/17.16 |
| 2012/0197401 A1* | 8/2012 | Duncan | A61F 2/4611 | 623/17.16 |
| 2012/0226358 A1* | 9/2012 | Kleiner | A61F 2/4465 | 623/17.16 |
| 2012/0277867 A1* | 11/2012 | Kana | A61F 2/4455 | 623/17.16 |
| 2012/0277872 A1* | 11/2012 | Kana | A61F 2/4465 | 623/17.16 |
| 2013/0073047 A1* | 3/2013 | Laskowitz | A61F 2/4455 | 623/17.16 |
| 2013/0096684 A1* | 4/2013 | Kleiner | A61F 2/4465 | 623/17.16 |
| 2013/0103153 A1* | 4/2013 | Blackwell | A61F 2/447 | 623/17.16 |
| 2013/0184825 A1* | 7/2013 | Kleiner | A61F 2/4465 | 623/17.16 |
| 2013/0218276 A1* | 8/2013 | Fiechter | A61F 2/4455 | 623/17.16 |
| 2013/0297029 A1* | 11/2013 | Kana | A61F 2/447 | 623/17.16 |
| 2013/0310935 A1* | 11/2013 | Swann | A61F 2/447 | 623/17.11 |
| 2014/0012384 A1* | 1/2014 | Kana | A61F 2/4465 | 623/17.16 |
| 2014/0025168 A1* | 1/2014 | Klimek | A61F 2/442 | 623/17.16 |
| 2014/0039623 A1* | 2/2014 | Iott | A61F 2/30744 | 623/17.16 |
| 2014/0046446 A1* | 2/2014 | Robinson | A61F 2/4611 | 623/17.16 |
| 2014/0088710 A1* | 3/2014 | Etminan | A61F 2/30744 | 623/17.16 |
| 2014/0121777 A1* | 5/2014 | Rosen | A61F 2/4455 | 623/17.16 |
| 2015/0073557 A1* | 3/2015 | Kleiner | A61F 2/4465 | 623/17.16 |
| 2015/0297358 A1* | 10/2015 | Perisic | A61F 2/4611 | 623/17.16 |

* cited by examiner

INTERBODY FUSION IMPLANT AND RELATED METHODS

CROSS-REFERENCE TO RELATED APPLICATIONS

The present application claims priority from U.S. Provisional Application Ser. No. 61/705,314, filed on Sep. 25, 2012, and entitled "Cage System" which is incorporated by reference herein in its entirety. The present application is related to U.S. patent application Ser. No. 12/834,855, filed on Jul. 12, 2010 and Ser. No. 13/920,483, filed Jun. 18, 2013, both applications entitled "Interbody Fusion Implant and Related Methods" and incorporated herein by reference in their entireties.

FIELD OF INVENTION

The present disclosure relates generally to the field of spinal orthopedics and more particularly to an interbody fusion implant system and method for assembling the system.

BACKGROUND

Intervertebral cages are well known. One known configuration is comprised of an endless, contiguous wall defining an interior space that is accessible from two opposite, open sides. The cage may be inserted between two adjacent vertebrae to maintain space between the vertebrae and promote fusion between the vertebrae. For example, the interior space may be filled with bone graft material or other biologic agents to facilitate boney fusion between the adjacent vertebrae.

Another known configuration includes two pieces that can be integrated to define a cage. An example of such a configuration is disclosed in Falahee, U.S. Patent Publication No. 2009/0030519, which alleges that devices according to the invention eliminate multiple steps, instruments, and trays, while being capable of a custom fit. The devices according to the invention permit easier and greater access to end plate surface area, and can be used with autografts, allografts, and biologics.

In U.S. patent application Ser. No. 12/834,855, now U.S. Pat. No. 8,491,658, the inventor of the present application has proposed a two piece cage design that includes a base member having three sidewalls and a closure member that is coupled to the base member to define a cage. As disclosed in U.S. patent application Ser. No. 12/834,855, a two-piece cage can include a generally elongated U-shaped base member having two opposing sidewalls each with a terminal, free end and a closure member that mates and preferably locks with the base member to define a cage. The base member and the closure member in a two-piece cage system includes mating parts that register with one another so that the two pieces may be assembled in-situ; i.e. during the operation.

A two-piece intervertebral cage can be made from a single material (e.g. a metal) or a composite material. The material selected for the cage will usually have a modulus of elasticity close to the modulus of elasticity of human bone and thus, relatively speaking, may be rather compliant. Thus, the base member in a two-piece cage system, which may be an elongated, U-shaped body, may be deformed when inserted into an intervertebral space especially when the base member is under pressure. Deformation of the base member is more pronounced when its length is longer than its width. Thus, the distance between the terminals, free ends of the sidewalls of the base member may vary when the base member is inserted in an intervertebral space.

In a lateral operation, depending on the type of retractor used, there tends to be some movement of the retractor in relation to the vertebral body and the disc. These movements and size limitations tend to cause a change in the shape of the base member also. There are limitations of exposure and size of possible annulotomy in the intervertebral disc annulus due to anatomical considerations such as location of neural structures, vessels, and muscle groups. In a lateral or anterolateral operation, the base member and the closure member of the cage are inserted through a long narrow retractor. Thus, the retractor makes the coupling of the closure member to the base member challenging in the presently available designs. The deformation of the base member of the cage, e.g. the change in the distance between the terminal free ends of the base member after it is inserted in place, causes a misalignment of the mating parts of the base member of the cage and its associated closure member making it more difficult for a surgeon to assemble the cage and complete the operation.

SUMMARY

An interbody fusion implant system according to the principles of the present disclosure includes a base member, a first guide, a second guide, and a closure member with a first thru-bore and a second thru-bore.

The base member includes a first side wall, a second side wall, and an end wall integrally coupled between respective distal ends of the first side wall and the second side wall and spacing the side walls to define an open trailing end coinciding with proximal ends of the side walls located opposite the distal ends thereof, and to define an interior bounded by the side walls and the end wall.

The first guide includes a first length and has a first portion attached to the proximal end of the first side wall and a second portion extending freely away from the first portion. The second guide includes a second length and has a first portion attached to the proximal end of the second side wall and a second portion extending freely away from the first portion.

The closure member is configured for assembly onto the second ends of the side walls of the base member to enclose the interior. The closure member includes a first thru-bore configured to be received by the first guide to align the closure member with the first side wall and a second thru-bore configured to be received by the second guide to align the closure member with the second side wall.

In other features, at least one of the first length and the second length is greater than or equal to 80 millimeters. In still other features, at least one of the first length and the second length is sufficient to enable assembly of the closure member onto the first and second guides outside a surgical site.

In still other features, at least one of the first portion and the second portion of the guides comprises a rigid portion. In still other features, at least one of the first portion and the second portion of the guides comprises a flexible portion. In still other features, the guides include cables and flexible rods.

In still other features, at least one of the first portions of the guides includes a locking mechanism to retain the closure member in contact with the proximal ends of the side walls.

In yet other features, at least one of the first portion and the second portion of at least one of the guides comprises a keyed profile that mates with a corresponding keyed profile of at least one of the thru-holes of the closure member.

In yet features, the first portion and the second portion of each guide comprise a rigid portion and a third portion linking the first portion and the second portion comprises a flexible portion.

A method for assembling an interbody fusion implant system includes the steps of providing a base member having a first side wall, a second side wall, and an end wall integrally coupled between respective distal ends of the first side wall and the second side wall and spacing the side walls to define an open trailing end coinciding with proximal ends of the side walls located opposite the distal ends thereof, and to define an interior bounded by the side walls and the end wall; inserting a first guide with a first length and attaching a first portion to the proximal end of the first side wall with a second portion extending freely away from the first portion; inserting a second guide with a second length and attaching a first portion to the proximal end of the second side wall with a second portion extending freely away from the first portion; and inserting a closure member onto the guides by inserting a first thru-bore over the first guide and a second thru-bore over the second guide, the first thru-bore configured to be received by the first guide to align the closure member with the first side wall and a second thru-bore configured to be received by the second guide to align the closure member with the second side wall, the closure member configured for assembly onto the second ends of the side walls of the base member to enclose the interior.

In other features, the step of inserting guides includes inserting guides wherein at least one of the first length and the second length is greater than or equal to 80 millimeters, at least one of the first length and the second length is sufficient to enable assembly of the closure member onto the first and second guides outside a surgical site, at least one of the first portion and the second portion of the guides comprises a rigid portion, or at least one of the first portion and the second portion of the guides comprises a flexible portion

DETAILED DESCRIPTION

Figure 1:
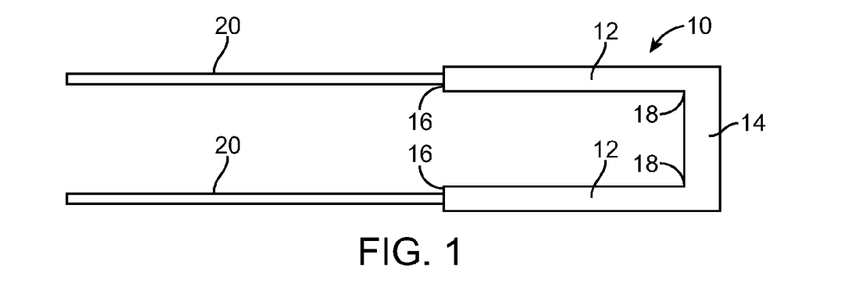
FIG. 1 depicts a top plan view of a base member of an exemplary interbody fusion implant system according to the principles of the present disclosure.

Referring to FIG. 1, a interbody fusion implant system according to the present disclosure includes a base member 10. Base member 10 may include a unitary body that includes two generally parallel side walls 12 and an end wall 14. Each side wall 12 includes a terminal, free end 16 and an end 18 opposite its free end 16. End wall 14 extends from one end 18 of one side wall 12 to another end 18 of the other side wall 12. In one example, base member 10 is a generally elongated U-shaped body, although other shapes may be employed without deviating from the scope and spirit of the present invention. In use, the side walls 12 may be disposed in an anterior or posterior position relative to the intervertebral space while the end wall 14 may be disposed in a lateral position relative to the intervertebral space. When inserted into the intervertebral space of a patient, the end wall 14 may be disposed distal to the surgeon.

According to an aspect of the present invention, an elongated guide 20 resides at and extends away from each terminal, free end 16. Preferably, each guide 20 is integrated with a respective one of the side walls 12. Thus, for example, the guide 20 may be screwed into a respective threaded orifice residing at a terminal, free end 16. Also, it should be noted that although it is possible to have each guide 20 reside at and extend from a terminal, free end 16, guides 20 may be positioned elsewhere as long as guides 20 function to align and register an closure member 22 to a base member 10 as further described below. For example, the guides 20 may be positioned anywhere along the side walls 12 within an interior space formed by the side walls 12 and end wall 14 or alternatively, outside the side walls 12.

Figure 2A:
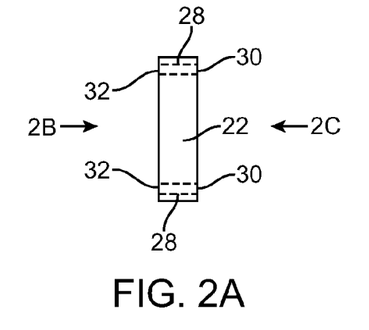
FIG. 2A depicts a top plan view of a closure member of an interbody fusion implant system according to the principles of the present disclosure.
Figure 2B:
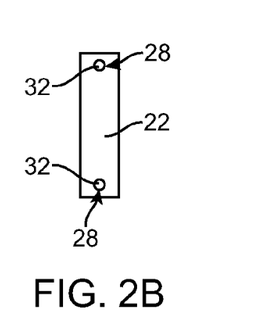
FIG. 2B depicts a side plan view of the closure member depicted in FIG. 2A, viewed in the direction of arrow 2B.
Figure 2C:
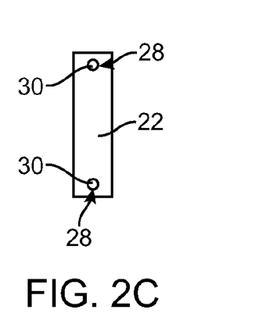
FIG. 2C depicts another side plan view of the closure member depicted in FIG. 2A, viewed in the direction of arrow 2C.

Referring now to FIGS. 2A-2C, a closure member 22 for a interbody fusion implant system according to the present disclosure includes features for receiving the guides 20. The closure member 22 may include a closure wall 24 that is at least wider than the distance between terminal, free ends 16 of base member 10, whereby, when closure member 22 is integrated (i.e. mated with, coupled to, and/or locked with) with base member 10, the two bodies form a body that surrounds an interior space for receiving material that promotes bone growth as further described below. The closure member 22 may be assembled in situ after packing the interior space with a bone graft material or other fusion promoting agents.

According to one aspect of the present invention, closure member 22 includes two elongated thru-bores 28 or channels, each defined to extend through the body of the closure member 22. Each channel 28 includes a first opening 30 and a second opening 32 opposite the first opening 30. Although the channels 28 appear to include a cylindrical profile with circular openings, the channels 28 may include any of various profiles that mate with the guides 20 as describe below.

Figure 3:
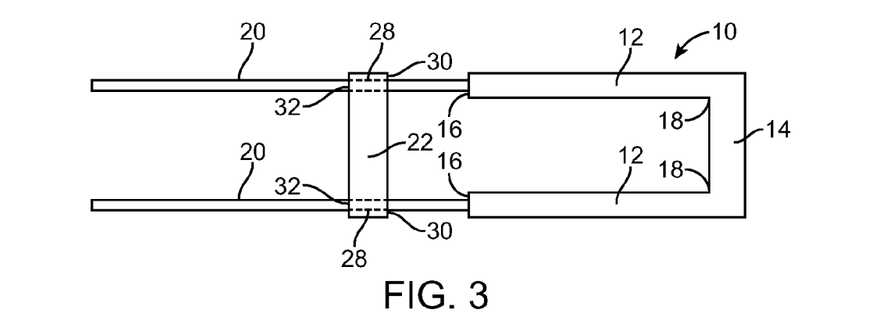
FIG. 3 depicts a closure member and a base member of an interbody fusion implant system according to the principles of the present disclosure in a partially assembled state.

Referring now to FIG. 3, each guide 20 is received inside a respective channel 28 at a respective first opening 30 and exits from the oppositely positioned second opening 32 as closure member 22 is moved toward base member 10, which, in practice, has been inserted in an intervertebral position. During insertion into the intervertebral space, the free ends 16 of the side walls 12 may deflect inwardly towards one another into the interior space of the cage system. The end wall 14 may deflect where the ends 18 meet the side walls 12. These deflections and deformations of the base member 10 may otherwise inhibit insertion of closure member 22. Thus, guides 20 may be provided to properly register and align closure member 22 with the base member 10.

Figure 4:
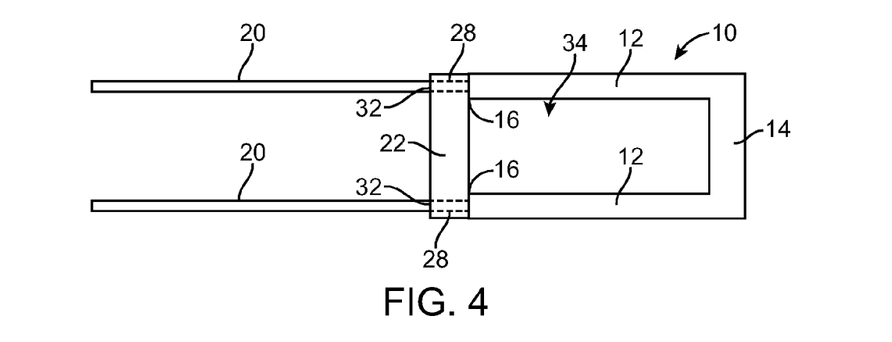
FIG. 4 depicts a closure member and a base member of an interbody fusion implant system according to the principles of the present disclosure in an assembled state.

As illustrated in FIG. 4, closure member 22 is further guided along guides 20 until closure member 22 mates with base member 10 to realize a cage. Note that in an assembled state, closure member 22 and base member 10 define an interior space 34 that can retain material for promoting bone growth as is known in the field. In use, the base member 10 may be inserted into the intervertebral space with guides 20 trailing behind. The guides 20 may extend outside of the patient. The interior space 34 may be packed with the material for promoting bone growth. The closure member 22 may be inserted on to the guides and guided along the guides 20 until reaching the free ends 22 of the base member 10.

Figure 5:
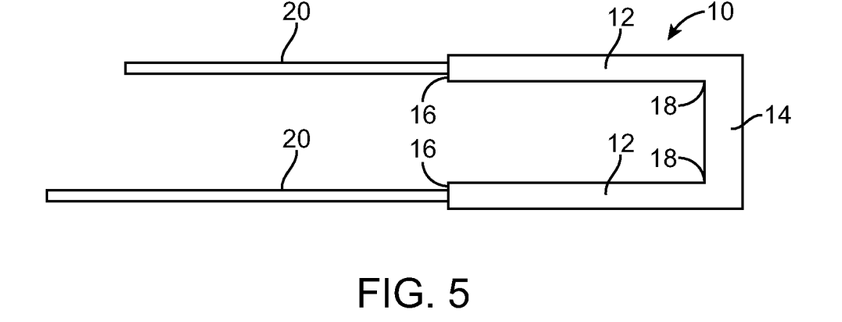
FIG. 5 depicts a top plan view of a base member for another exemplary interbody fusion implant system according to the principles of the present disclosure.

Referring now to FIG. 5, in other features, the guides 20 of base member 10 may have different lengths. Different lengths may be provided to accommodate varying patient anatomies, surgical approaches, and various other considerations. Also, each guide 20 may have a differently shaped cross-section for proper alignment of closure member 22 with a base member 10, which has already been inserted. For example, one or more guides 20 may be keyed to match mating channels 28 of the closure member 22 as described below.

Figure 6:
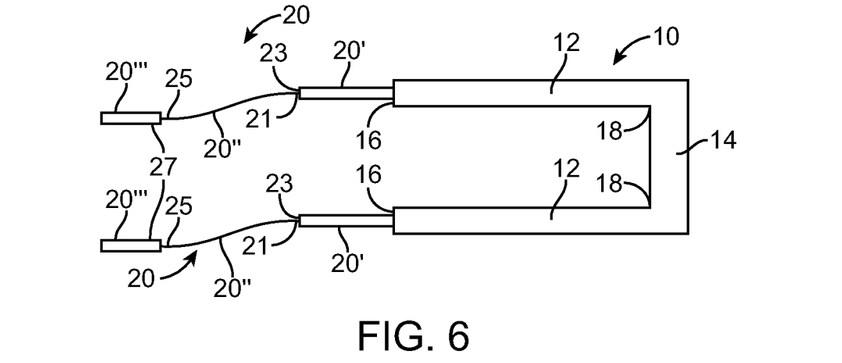
FIG. 6 depicts a top plan view of a base member for another interbody fusion implant system according to the principles of the present disclosure.

Referring now to FIG. 6, in still other features, at least one guide 20 may include a first rigid portion 20' residing at the terminal, free end 16 of the base member 10. A flexible portion 20" may include a distal end 21 attached to a proximal end 23 of the first rigid portion 20'. A second rigid portion 20''' may include a distal end 27 attached to a proximal end 25 of the flexible portion 20" to aid in insertion of flexible portion 20" into a respective channel 28. Flexible portion 20" may be a cable, a flexible rod, or the like. For example, the first rigid portion 20' and second rigid portion 20''' may be linked by the third flexible portion 20".

Figure 7:
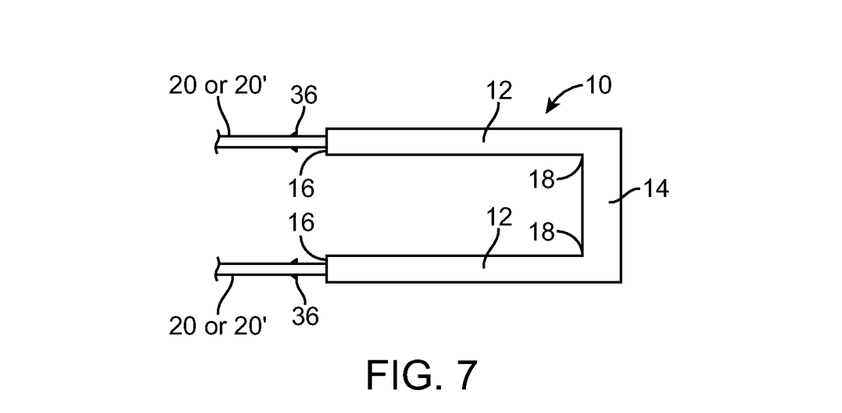
FIG. 7 depicts a top plan view of a base member for another exemplary interbody fusion implant system according to the principles of the present disclosure.

Referring now to FIG. 7, in still other features, at least one 20 or 20' may be provided with a feature that can serve as part of a locking mechanism. Thus, for example, projections 36 (e.g. hooks or spikes) may be provided on each guide 20 at a location that would reside within the channel 28 or outside the opening 32 once the guide 20 is fully inserted through the closure member 22. Each projection may be dimensioned so that it anchors into the interior surface of the channel 28, whereby closure member 22 cannot be retracted once it is fully assembled. Note, for example, the tips of projections 36 would be aligned away from the closure member 22 and toward base member 10. Thus, once fully assembled, the closure member 22 would be integrated with base member 10. At least the portion of each guide 20 that would extend beyond the boundaries of the closure member 22 should be configured so that it may be readily severed once the cage is fully assembled.

Referring back to FIGS. 2A-2C, each channel 28 may have an oval cross-section (transverse to its longitudinal axis) and may be sized to make contact with the exterior surface of a respective guide 20, whereby guides 20 and channels 28 slidably engage one another. Preferably, the cross-section (transverse to its longitudinal axis) of each guide 20 would have the same shape as the cross-section of the channel 28 in which it is received; however, such is not a necessity. It should be noted that the guide 20 may have a cross-section other than oval. For example, circular, square, triangular, rectangular, star-shaped, or any other shape would be within the scope of the present invention. As described above, at least one of the guides 20 may be keyed and at least one of the channels 28 may be keyed such that the closure member 22 may be inserted in a particular orientation.

For example, in some features, the base member 10 may include a first of the side walls 12 with a first height and a second of the side walls 12 with a second height 12. The first height may be greater than the second height to provide curvature such as a lordotic curvature associated with the lumbar region of the spine. The closure member 22 may likewise be configured to include a first height at one end corresponding to the first height of the first of the side walls 12 and a second height at the other end corresponding to the second height of the second of the side walls 12. Therefore, the closure member may need to be inserted in a particular orientation to match the corresponding heights of the closure member 22 with the heights of the side walls 12.

It can be appreciated by the skilled person, that in addition to guides 20, a cage system according to the present invention can include a locking mechanism to integrate closure member 22 and base member 10. The locking mechanism may be in place of or in addition to any projections 36, hooks, and the like as describe above. Examples of various locking mechanisms are disclosed in U.S. patent application Ser. No. 12/834,855 (Appendix A).

Figure 8:
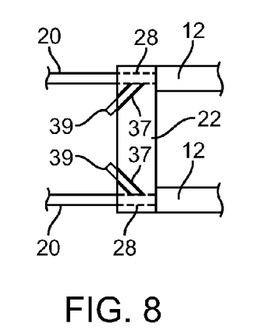
FIG. 8 depicts a top plan view of a locking arrangement for securing a closure member to a base member.

FIG. 8 illustrates one locking configuration, which may be employed. In this configuration, threaded channels 37 are defined in the body of closure member 22. Each threaded channel is configured to have an opening in communication with each channel 28, and another opposite opening through which a screw 39 or the like is threadably receivable. In use, screws 39 are threadably received in channel 37 and abut guides 20 when sufficiently inserted, whereby closure member 22 is secured to guides 20.

Figure 9A:
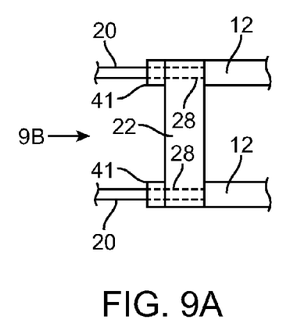
FIG. 9A depicts a top plan view of another locking arrangement for securing a base member to a closure member.
Figure 9B:
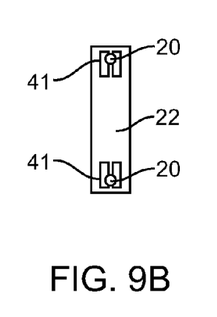
FIG. 9B shows a side plan view of the arrangement of FIG. 9A in the direction of arrow 9B.

Referring to FIGS. 9A and 9B, in another configuration, once closure member 22 is in proper position (i.e. is in contact with base member 10) clips 41 are attached to portions of guides 20 that extend out of closure member 22, in order to secure closure member 22 to base member 10.

Figure 10:
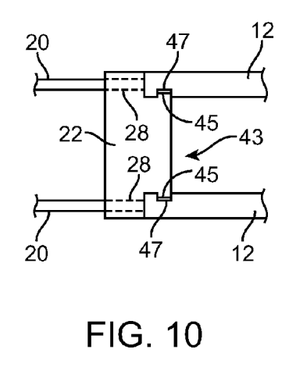
FIG. 10 depicts a further locking arrangement for securing a closure member to a base member.

Referring to FIG. 10, closure member 22 may be configured to have a portion 43 that is receivable between side walls 12 of base member 10. Portion 43 may include two oppositely disposed teeth 45 or projections. Each tooth 45 is receivable in a corresponding recess 47 defined in an interior surface of a respective side wall 12, for example near the free ends 16. Once teeth 45 are received in recesses 47, closure member 22 is secured to base member 10 to define a cage. The free ends 16 may be sloped or others shaped to ease insertion of the teeth 45 past the free ends 16 and into the recesses 47.

Figure 11:
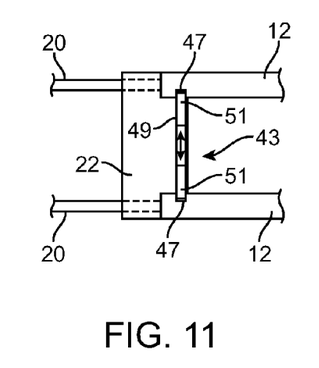
FIG. 11 depicts yet another locking arrangement for securing a closure member to a base member.

Referring now to FIG. 11, instead of teeth 45, closure member 22 may include a channel 49 that is oriented in a direction generally transverse to the direction of elongation of guides 20. Received inside channel 49 are two pins 51 configured to be slidably urged toward sidewalls 12 of base member 10, until the tips of pins 51 are received in recesses 47, whereby base member 10 and closure member 22 are secured to one another to define a cage. Note that the double-arrow indicates the direction of motion of pins 51 in order to realize locking as described herein. In order to urge pins 51 in the described direction pins 51 may be spring-loaded, or a mechanism such as a mechanism shown in pending U.S. patent application Ser. No. 12/834,855 may be used.

A suitable material for making a cage according to the present invention may be PEEK (polyether ether ketone), titanium or a titanium alloy, or carbon fiber. Guides 20 may be made from titanium, tantalum, stainless steel, or any other suitable metal alloy. Preferably, a cage system according to the present invention is made of a combination of different materials. For example, base member 10 and closure member 22 (together constituting the cage part) may be made of PEEK, while guides 20 and the feature constituting the locking mechanism may be made of titanium.

The cage part of the system may be 16 mm to 28 mm wide and 45 mm to 65 mm long in its assembled state. The height of the cage part may be 8 to 16 mm. The shape of base member 10 can be lordotic in nature so that the anterior piece is taller than the posterior as described above. Base member 10 could also be biconvex so as to accommodate the anatomy of the vertebral body.

Guides 20 may be from 80 mm to 180 mm long. The length of guides 20 would depend on which side of the patient is to receive the cage system. It should be noted that while guides 20 are shown to be assembled onto base member 10, guides 20 and base member 10 could be configured so that guides 20 could be assembled in situ. Thus, for example, base member 10 could be inserted in place followed by the installment of guides 20 into previously drilled holes in base member 10. Alternatively, the surgeon could judge how long guides 20 should be, and select and install the right length before inserting base member 10. Therefore, in a cage system according to present invention, a guide 20 can be fully integrated with base member 10 such that it cannot be removed, or a guide 20 can be configured for integration in situ so that it can be installed in situ, removed after base member 10 is inserted, or left in place.

As will be understood by a skilled person, base member 10 and closure member 22 are inserted in place using an appropriate inserter. One suitable inserter for inserting base member 10 can include a locking mechanism that frictionally couples with guides 20 of base member 10. Once base member 10 is inserted in place, the lock may be disengaged to detach the inserter from base member 10 so that the inserter may be withdrawn. Another suitable inserter could include a feature that can be expanded inside base member 10 and frictionally couple to the interior surfaces of the sidewalls of base member 10. Once base member 10 is inserted, the inserter may be detached by decoupling the inserter from base member 10. In either case, the inserter would be detachably secured to base member 10 so that it may be used to insert base member 10 in place, and detached and withdrawn once insertion is completed. An inserter for inserting closure member 22 would also be devised to be detachably secured to closure member 22 for the same reasons outlined herein.

Figure 12:
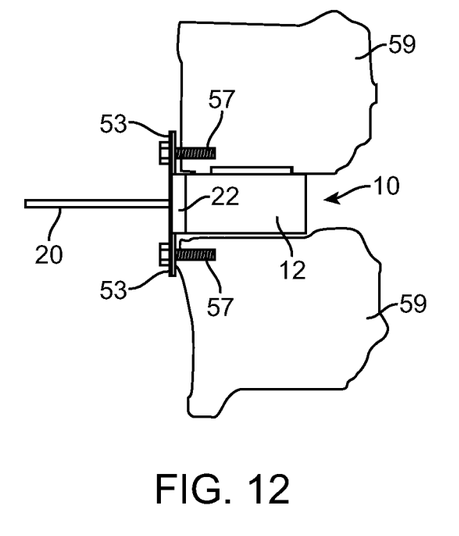
FIG. 12 depicts a cage system in its assembled state inserted in place before removal of the guides.
Figure 13:
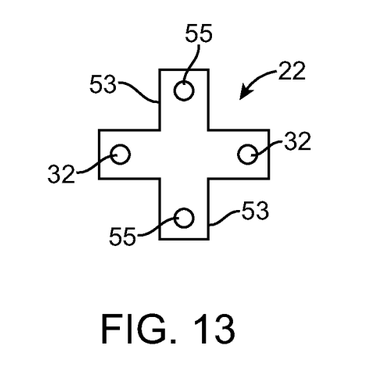
FIG. 13 depicts a top plan view of a closure member with mounting extensions extending from opposite edges of the enclosure wall portion of the closure member.

FIG. 12 depicts a cage system according to the present invention inserted in place between two vertebrae 59 before guides 20 are severed. In the variation disclosed in FIG. 12 closure member 22 is provided with two extensions 53 each extending from an opposite edge of the enclosure wall portion of closure member 22 (see FIG. 13). As illustrated in FIG. 13, each extension 53 is provided with an eyelet 55 that is intended to receive a screw 57 or the like mounting hardware as illustrated in FIG. 12, whereby the cage system may be further secured to vertebrae 59 once screws 57 are anchored therein.

While the cage systems disclosed herein are particularly suited for lateral applications, the cage systems may also be employed in anterior applications.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

The invention claimed is:

1. An interbody fusion implant system for use in lateral access spinal surgery, comprising:
   a base member having a first side wall, a second side wall, and an end wall integrally coupled between respective distal ends of the first side wall and the second side wall and spacing the side walls to define an open trailing end coinciding with proximal ends of the side walls located opposite the distal ends thereof, and to define an interior bounded by the side walls and the end wall;
   a first guide with a first length and having a first portion attached to the proximal end of the first side wall and a second portion extending freely away from the first portion;
   a second guide with a second length and having a first portion attached to the proximal end of the second side wall and a second portion extending freely away from the first portion; and
   a closure member configured for assembly onto the second ends of the side walls of the base member to enclose the interior, the closure member including
      a first thru-bore configured to be received by the first guide to align the closure member with the first side wall;
      a second thru-bore configured to be received by the second guide to align the closure member with the second side wall;
      a first threaded channel extending in a medial to lateral trajectory from a surface of the closure member into the first thru-bore; and
      a second threaded channel extending in a medial to lateral trajectory from the surface of the closure member into the second thru-bore, the first threaded channel and the second threaded channel configured to receive a first screw and a second screw so as to secure the closure member to respective first guide and second guide.

2. The system of claim 1, wherein at least one of the first length and the second length is greater than or equal to 80 millimeters.

3. The system of claim 1, wherein at least one of the first length and the second length is sufficient to enable assembly of the closure member onto the first and second guides outside a surgical site.

4. The system of claim 1, wherein the at least one of the first portion and the second portion of the guides comprises a rigid portion.

5. The system of claim 1, wherein the at least one of the first portion and the second portion of the guides comprises a flexible portion.

6. The system of claim 1, wherein at least one of the first portions of the guides includes a locking mechanism to retain the closure member in contact with the proximal ends of the side walls.

7. The system of claim 1, wherein at least one of the first portion and the second portion of at least one of the guides comprises a keyed profile that mates with a corresponding keyed profile of at least one of the thru-holes of the closure member.

8. The system of claim 1, wherein the guides comprise guide cables.

9. The system of claim 1, wherein the guides comprise flexible rods.

10. The system of claim 1, wherein the first portion and the second portion of each guide comprise a rigid portion and a third portion linking the first portion and the second portion comprises a flexible portion.

11. A method for assembling an interbody fusion implant system, comprising:

providing a base member having a first side wall having a first opening disposed on a proximal end of the first side wall, a second side wall having a second opening disposed on a proximal end of the second side wall, and an end wall integrally coupled between respective distal ends of the first side wall and the second side wall and spacing the side walls to define an open trailing end coinciding with proximal ends of the side walls located opposite the distal ends thereof, and to define an interior bounded by the side walls and the end wall;

inserting a first guide with a first length and attaching a first portion to the first opening of the proximal end of the first side wall with a second portion extending freely away from the first portion;

inserting a second guide with a second length and attaching a first portion to the second opening of the proximal end of the second side wall with a second portion extending freely away from the first portion; and providing a closure member having a first thru-bore opposite a second thru-bore, inserting the first thru-bore and the second thru-bore of closure member onto the second portion of the first guide and the second portion of the second guide respectively, and sliding the closure member along the first guide and the second guide and pressing the closure member against the first side wall and second side wall.

12. The method of claim 11, wherein at least one of the first length and the second length is greater than or equal to 80 millimeters.

13. The system of claim 11, wherein at least one of the first length and the second length is sufficient to enable assembly of the closure member onto the first and second guides outside a surgical site.

14. The system of claim 11, wherein the at least one of the first portion and the second portion of the guides comprises a rigid portion.

15. The system of claim 11, wherein the at least one of the first portion and the second portion of the guides comprises a flexible portion.

* * * * *